(12) United States Patent
Breslav et al.

(10) Patent No.: US 7,897,636 B2
(45) Date of Patent: Mar. 1, 2011

(54) SULFAMIDE DERIVATIVE USEFUL FOR THE TREATMENT OF EPILEPSY

(75) Inventors: Michael Breslav, Maple Glen, PA (US); Brian Klein, Salt Lake City, UT (US); Xun Li, New Hope, PA (US); John A. Moyer, New Hope, PA (US); Frank J. Villani, Perkasie, PA (US)

(73) Assignee: Janssen Pharmaceutica NV (BE)

( * ) Notice: Subject to any disclaimer, the term of this patent is extended or adjusted under 35 U.S.C. 154(b) by 0 days.

(21) Appl. No.: 12/187,797

(22) Filed: Aug. 7, 2008

(65) Prior Publication Data

US 2009/0176865 A1 Jul. 9, 2009

Related U.S. Application Data

(60) Provisional application No. 60/954,676, filed on Aug. 8, 2007.

(51) Int. Cl.
*A61K 31/38* (2006.01)
*A61K 31/16* (2006.01)
*A01N 43/06* (2006.01)
*A01N 41/02* (2006.01)

(52) U.S. Cl. ...................... 514/446; 514/600
(58) Field of Classification Search .............. None
See application file for complete search history.

(56) References Cited

U.S. PATENT DOCUMENTS

2006/0047001 A1 * 3/2006 Parker et al. ............ 514/419

FOREIGN PATENT DOCUMENTS

WO 2006/023861 3/2006
WO 2007/098486 8/2007

OTHER PUBLICATIONS

Swinyard EA, Woodhead JH, White HS, Franklin MR. Experimental selection, quantification, and evaluation of anticonvulsants. In Levy RH, et al., eds. *Antiepileptic Drugs.* $3^{rd}$ ed. New York: Raven Press, 1989:85-102.
Duggan et al., "Identification of the biologically active form of sulindac" Journal of Pharmacology and Experimental Therapeutics, American Society for Pharmacology and Experimental Therapeutics, US, vol., 201, No, 1, 1977, pp. 8-13.
International Search Report re: PCT/US2008/072509 dated Nov. 5, 2008.

* cited by examiner

*Primary Examiner*—Leslie A. Royds

(57) ABSTRACT

The present invention is directed to novel sulfamide derivatives, pharmaceutical compositions comprising said compounds and methods for the treatment of epilepsy and related disorders comprising administering to a subject in need thereof, said compounds, either alone or as co-therapy with one or more anticonvulsant and/or anti-epileptic agents.

15 Claims, No Drawings

SULFAMIDE DERIVATIVE USEFUL FOR THE TREATMENT OF EPILEPSY

CROSS REFERENCE TO RELATED APPLICATIONS

This application claims the benefit of U.S. Provisional Application 60/954,676, filed on Aug. 8, 2007, which is incorporated by reference herein in its entirety.

FIELD OF THE INVENTION

The present invention is directed to novel sulfamide derivatives, pharmaceutical compositions comprising said compounds and methods for the treatment of epilepsy and related disorders comprising administering to a subject in need thereof, said compounds, either alone or as co-therapy with one or more anticonvulsant and/or anti-epileptic agents.

BACKGROUND OF THE INVENTION

Epilepsy describes a condition in which a person has recurrent seizures due to a chronic, underlying process. Epilepsy refers to a clinical phenomenon rather than a single disease entity, since there are many forms and causes of epilepsy. Using a definition of epilepsy as two or more unprovoked seizures, the incidence of epilepsy is estimated at approximately 0.3 to 0.5 percent in different populations throughout the world, with the prevalence of epilepsy estimated at 5 to 10 people per 1000.

An essential step in the evaluation and management of a patient with a seizure is to determine the type of seizure that has occurred. The main characteristic that distinguishes the different categories of seizures is whether the seizure activity is partial (synonymous with focal) or generalized.

Partial seizures are those in which the seizure activity is restricted to discrete areas of the cerebral cortex. If consciousness is fully preserved during the seizure, the clinical manifestations are considered relatively simple and the seizure is termed a simple-partial seizure. If consciousness is impaired, the seizure is termed a complex-partial seizure. An important additional subgroup comprises those seizures that begin as partial seizures and then spread diffusely throughout the cortex, which are known as partial seizures with secondary generalization.

Generalized seizures involve diffuse regions of the brain simultaneously in a bilaterally symmetric fashion. Absence or petit mal seizures are characterized by sudden, brief lapses of consciousness without loss of postural control. Atypical absence seizures typically include a longer duration in the lapse of consciousness, less abrupt onset and cessation, and more obvious motor signs that may include focal or lateralizing features. Generalized Tonic-clonic or grand mal seizures, the main type of generalized seizures, are characterized by abrupt onset, without warning. The initial phase of the seizure is usually tonic contraction of muscles, impaired respiration, a marked enhancement of sympathetic tone leading to increased heart rate, blood pressure, and pupillary size. After 10-20 s, the tonic phase of the seizure typically evolves into the clonic phase, produced by the superimposition of periods of muscle relaxation on the tonic muscle contraction. The periods of relaxation progressively increase until the end of the ictal phase, which usually lasts no more than 1 min. The postictal phase is characterized by unresponsiveness, muscular flaccidity, and excessive salivation that can cause stridorous breathing and partial airway obstruction. Atonic seizures are characterized by sudden loss of postural muscle tone lasting 1-2 s. Consciousness is briefly impaired, but there is usually no postictal confusion. Myoclonic seizures are characterized by a sudden and brief muscle contraction that may involve one part of the body or the entire body.

There remains a need to provide an effective treatment for epilepsy and related disorders.

SUMMARY OF THE INVENTION

The present invention is directed to an isolated form of a compound of formula (A)

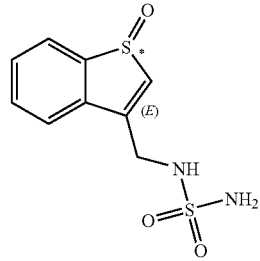

(A)

and enantiomers and pharmaceutically acceptable salts thereof. In an embodiment, the present invention is directed to an isolated form of the (R) enantiomer of the compound of formula (A). In another embodiment, the present invention is directed to an isolated form of the (S) enantiomer of the compound of formula (A). In additional embodiments, the present invention is directed to an isolated form of a compound selected from the group consisting of pharmaceutically acceptable salts of the compound of formula (A), pharmaceutically acceptable salts of the (R) enantiomer of the compound of formula (A) and pharmaceutically acceptable salts of the (S) enantiomer of the compound of formula (A).

In an embodiment, the present invention is directed to an isolated form of the (+) enantiomer of the compound of formula (A), as measured according to the conditions a described in Example 3, which follows herein. In another embodiment, the present invention is directed to an isolated form the (−) enantiomer of the compound of formula (A), as measured according to the conditions a described in Example 3, which follows herein. In additional embodiments, the present invention is directed to an isolated form of a compound selected from the group consisting of pharmaceutically acceptable salts of the compound of formula (A), pharmaceutically acceptable salts of the (+) enantiomer of the compound of formula (A) and pharmaceutically acceptable salts of the (−) enantiomer of the compound of formula (A).

The present invention is further directed to a method for the treatment of epilepsy and related disorders, comprising administering to a subject in need thereof, a therapeutically effective amount of (a) an isolated form of a compound of formula (A) or pharmaceutically acceptable salt thereof; or (b) an isolated form of an enantiomer of the compound of formula (A) or pharmaceutically acceptable salt thereof.

The present invention is further directed to a method for the treatment of epilepsy and related disorders comprising administering to a subject in need thereof, a therapeutically effective amount of co-therapy comprising (a) an isolated form of a compound of formula (A) or pharmaceutically acceptable salt thereof or an isolated form of an enantiomer of the compound of formula (A) or pharmaceutically acceptable salt thereof and (b) one or more anticonvulsant or anti-epileptic agents.

The present invention is further directed to a process for the preparation and/or isolation of any of the compounds describe herein, according to any of the procedures described herein. The present invention is further directed to a product prepared according to any of the processes or procedures described herein.

DETAILED DESCRIPTION OF THE INVENTION

The present invention is directed to an isolated form of a compound of formula (A)

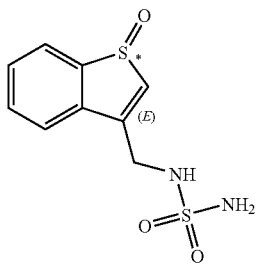

(A)

also known as N-[(1-oxidobenzo[b]thien-3-yl)methyl]-sulfamide, and optical isomers (i.e enantiomers) and pharmaceutically acceptable salts thereof, useful for the treatment of epilepsy and related disorders, alone or as co-therapy with one or more anticonvulsant or anti-epileptic agents.

The compound of formula (A), as defined herein, shall include all possible mixtures of the corresponding (R) and (S) enantiomers of the compound of formula (A). The compound of formula (A), as defined herein, shall further include all possible mixtures of the corresponding (+) and (−) enantiomers of the compound of formula (A).

In an embodiment, the present invention is directed to an isolated form of the (R) enantiomer of the compound of formula (A), hereinafter referred to as a compound of formula (A-R)

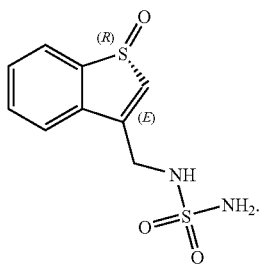

(A-R)

In another embodiment, the present invention is directed to an isolated form of the (S) enantiomer of the compound of formula (A), hereinafter referred to as a compound of formula (A-S)

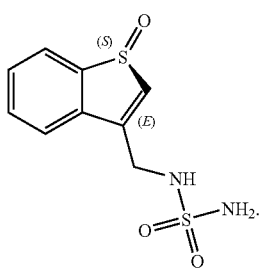

(A-S)

In additional embodiments, the present invention is directed to pharmaceutically acceptable salts of the compound of formula (A-R) and the compound of formula (A-S).

In an embodiment, the present invention is directed to an isolated form of the (+) enantiomer of the compound of formula (A). In an embodiment, the present invention is directed to an isolated form of the (−) enantiomer of the compound of formula (A). In additional embodiments, the present invention is directed to pharmaceutically acceptable salts of the (+) and (−) enantiomers of the compound of formula (A).

The compound of formula (A) and its corresponding enantiomers are metabolites of the compound of formula (P)

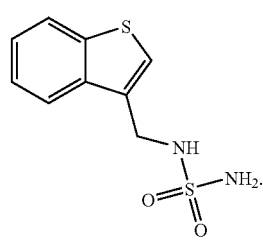

(P)

The compound of formula (A) and its corresponding enantiomers may alternatively convert to the compound of formula (P), for example on administration to mice.

The compound of formula (P) is an example of the novel sulfamate derivatives described in US Patent Publication 2006/0047001 A1, which derivatives are useful for the treatment of epilepsy and related disorders. Said sulfamate derivatives, including the compound of formula (P), are further useful (alone and/or as co-therapy in combination with one or more pharmaceutical agents) for the treatment of bipolar depression, bipolar disorder and mania; for the treatment of depression; for the treatment of epileptogensis; for the treatment of glucose related disorders and lipid related disorders; for the treatment and/or prevention of migraine; for neuroprotection, the treatment of acute and chronic neurodegenerative disorders and for the prevention of neuron death or damage following brain, head or spinal cord trauma or injury; for the treatment of pain; and for the treatment of substance abuse and addiction.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

In an embodiment of the present invention, the isolated form of the compound of formula (A-R) is present in an enantiomeric excess of greater than or equal to about 50%. In another embodiment of the present invention, the isolated form of the compound of formula (A-R) is present in an enantiomeric excess of greater than or equal to about 75%. In another embodiment of the present invention, the isolated form of the compound of formula (A-R) is present in an enantiomeric excess of greater than or equal to about 85%. In another embodiment of the present invention, the isolated form of the compound of formula (A-R) is present in an enantiomeric excess of greater than or equal to about 90%. In another embodiment of the present invention, the isolated form of the compound of formula (A-R) is present in an enantiomeric excess of greater than or equal to about 95%. In another embodiment of the present invention, the isolated form of the compound of formula (A-R) is present in an enantiomeric excess of greater than or equal to about 98%. In another embodiment of the present invention, the isolated form of the compound of formula (A-R) is present in an enantiomeric excess of greater than or equal to about 99%.

In an embodiment of the present invention, the isolated form of the compound of formula (A-S) is present in an enantiomeric excess of greater than or equal to about 50%. In another embodiment of the present invention, the isolated form of the compound of formula (A-S) is present in an enantiomeric excess of greater than or equal to about 75%. In another embodiment of the present invention, the isolated form of the compound of formula (A-S) is present in an enantiomeric excess of greater than or equal to about 85%. In another embodiment of the present invention, the isolated form of the compound of formula (A-S) is present in an enantiomeric excess of greater than or equal to about 90%. In another embodiment of the present invention, the isolated form of the compound of formula (A-S) is present in an enantiomeric excess of greater than or equal to about 95%. In another embodiment of the present invention, the isolated form of the compound of formula (A-S) is present in an enantiomeric excess of greater than or equal to about 98%. In another embodiment of the present invention, the isolated form of the compound of formula (A-S) is present in an enantiomeric excess of greater than or equal to about 99%.

In an embodiment of the present invention, the isolated form of the compound of formula (+) is present in an enantiomeric excess of greater than or equal to about 50%. In another embodiment of the present invention, the isolated form of the compound of formula (+) is present in an enantiomeric excess of greater than or equal to about 75%. In another embodiment of the present invention, the isolated form of the compound of formula (+) is present in an enantiomeric excess of greater than or equal to about 85%. In another embodiment of the present invention, the isolated form of the compound of formula (+) is present in an enantiomeric excess of greater than or equal to about 90%. In another embodiment of the present invention, the isolated form of the compound of formula (+) is present in an enantiomeric excess of greater than or equal to about 95%. In another embodiment of the present invention, the isolated form of the compound of formula (+) is present in an enantiomeric excess of greater than or equal to about 98%. In another embodiment of the present invention, the isolated form of the compound of formula (+) is present in an enantiomeric excess of greater than or equal to about 99%.

In an embodiment of the present invention, the isolated form of the compound of formula (−) is present in an enantiomeric excess of greater than or equal to about 50%. In another embodiment of the present invention, the isolated form of the compound of formula (−) is present in an enantiomeric excess of greater than or equal to about 75%. In another embodiment of the present invention, the isolated form of the compound of formula (−) is present in an enantiomeric excess of greater than or equal to about 85%. In another embodiment of the present invention, the isolated form of the compound of formula (−) is present in an enantiomeric excess of greater than or equal to about 90%. In another embodiment of the present invention, the isolated form of the compound of formula (−) is present in an enantiomeric excess of greater than or equal to about 95%. In another embodiment of the present invention, the isolated form of the compound of formula (−) is present in an enantiomeric excess of greater than or equal to about 98%. In another embodiment of the present invention, the isolated form of the compound of formula (−) is present in an enantiomeric excess of greater than or equal to about 99%.

As used herein, unless otherwise noted, the term "isolated form" shall mean that the compound is present, in any solid form or mixture, outside of a living animal, preferably outside of a human body. In an embodiment, the present invention is directed to an isolated form of any of the compounds described herein.

As used herein, unless otherwise noted, the term "substantially pure compound" shall mean that the mole percent of impurities in the isolated compound, including but not limited to the compound of formula (P), is less than about 5 mole percent, preferably less than about 2 mole percent, more preferably, less than about 0.5 mole percent, most preferably, less than about 0.1 mole percent. In another alternative embodiment of the present invention, any of the compounds described herein are substantially pure.

As used herein, unless otherwise noted, the terms "substantially free of a corresponding salt form(s)" and "substantially pure free base" when used to described any of the compounds disclosed herein shall mean that the mole percent of any corresponding salt form(s) in the isolated compound is less than about 5 mole percent, preferably less than about 2 mole percent, more preferably, less than about 0.5 mole percent, most preferably less than about 0.1 mole percent. In another alternative embodiment of the present invention, any of the compounds described herein is substantially free of corresponding salt forms.

In an embodiment of the present invention, the isolated form of the compound of formula (A), the isolated form of the compound of formula (A-R), the isolated form of the compound of formula (A-S), the isolated form of the (+) enantiomer of the compound of formula (A) or the isolated form of the (−) enantiomer of the compound of formula (A), is present as a substantially pure compound. In another embodiment of the present invention, the isolated form of the compound of formula (A), the isolated form of the compound of formula (A-R), the isolated form of the compound of formula (A-S), the isolated form of the (+) enantiomer of the compound of formula (A) or the isolated form of the (−) enantiomer of the compound of formula (A), is present in a form which is substantially free of any corresponding salt form(s). In another embodiment of the present invention, the isolated form of the compound of formula (A), the isolated form of the compound of formula (A-R), the isolated form of the compound of formula (A-S), the isolated form of the (+) enantiomer of the compound of formula (A) or the isolated form of the (−) enantiomer of the compound of formula (A), is present as its corresponding pharmaceutically acceptable salt.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

As used herein, unless otherwise noted, the terms "epilepsy and related disorders" or "epilepsy or related disorder" shall mean any disorder in which a subject (preferably a human adult, child or infant) experiences one or more seizures and/or tremors. Suitable examples include, but are not limited to, epilepsy (including, but not limited to, localization-related epilepsies, generalized epilepsies, epilepsies with both generalized and local seizures, and the like), seizures associated with Lennox-Gastaut syndrome, seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, fever, infection, and the like), essential tremor, restless limb syndrome, and the like. Preferably, the disorder is selected from epilepsy (regardless of type, underlying cause or origin), essential tremor or restless limb syndrome, more preferably, the disorder is epilepsy (regardless of type, underlying cause or origin) or essential tremor.

The term "subject" as used herein, refers to an animal, preferably a mammal, most preferably a human adult, child or infant, who has been the object of treatment, observation or experiment.

As used herein, the term "composition" is intended to encompass a product comprising the specified ingredients in the specified amounts, as well as any product which results, directly or indirectly, from combinations of the specified ingredients in the specified amounts.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of one or more of the symptoms of the disease or disorder being treated; and/or reduction of the severity of one or more of the symptoms of the disease or disorder being treated.

Wherein the present invention is directed to co-therapy or combination therapy, comprising administration of an isolated form of a compound of formula (A), or an isolated form of an enantiomer of the compound of formula (A) or pharmaceutically acceptable salt thereof and one or more anticonvulsant or anti-epileptic agents, therapeutically effective amount shall mean that amount of the combination of agents taken together so that the combined effect elicits the desired biological or medicinal response. For example, the therapeutically effective amount of co-therapy comprising administration of an isolated form of a compound of formula (A), or an isolated form of an enantiomer of the compound of formula (A) or pharmaceutically acceptable salt thereof and at least one suitable anti-epileptic agent would be the amount of the isolated form of the compound of formula (A), or the isolated form of an enantiomer of the compound of formula (A) or pharmaceutically acceptable salt thereof and the amount of the suitable anti-epileptic agent that when taken together or sequentially have a combined effect that is therapeutically effective. Further, it will be recognized by one skilled in the art that in the case of co-therapy with a therapeutically effective amount, as in the example above, the amount of the isolated form of the compound of formula (A) or the isolated form of an enantiomer of the compound of formula (A) or pharmaceutically acceptable salt thereof and/or the amount of the suitable anti-epileptic agent individually may or may not be therapeutically effective.

As used herein, the terms "co-therapy" and "combination therapy" shall mean treatment of a subject in need thereof by administering one or more anticonvulsant and/or anti-epileptic agent(s) and an isolated form of a compound of formula (A), or an isolated form of an enantiomer of the compound of formula (A) or pharmaceutically acceptable salt thereof, wherein the isolated form of the compound of formula (A), or the isolated form of an enantiomer of the compound of formula (A) or pharmaceutically acceptable salt thereof and the anticonvulsant and/or anti-epileptic agent(s) are administered by any suitable means, simultaneously, sequentially, separately or in a single pharmaceutical formulation. Where the isolated form of the compound of formula (A), or the isolated form of an enantiomer of the compound of formula (A) or pharmaceutically acceptable salt thereof and the anticonvulsant and/or anti-epileptic agent(s) are administered in separate dosage forms, the number of dosages administered per day for each compound may be the same or different. The isolated form of the compound of formula (A), or the isolated form of an enantiomer of the compound of formula (A) or pharmaceutically acceptable salt thereof and the anticonvulsant and/or anti-epileptic agent(s) may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The isolated form of the compound of formula (A), or isolated form of an enantiomer of the compound of formula (A) or pharmaceutically acceptable salt thereof and the anticonvulsant and/or anti-epileptic agent(s) may be administered according to simultaneous or alternating regimens, at the same or different times during the course of the therapy, concurrently in divided or single forms.

As used herein, unless otherwise noted, the term "antiepileptic agent" and the abbreviation "AED" will be used interchangeably with the term "anti-convulsant agent," and as used herein, refer to an agent capable of treating, inhibiting or preventing seizure activity or ictogenesis when the agent is administered to a subject or patient.

Suitable examples of anti-convulsant and/or anti-epileptic agents include, but are not limited to:

(a) AMPA antagonists such as AMP-397, E-2007, NS-1209, talampanel, and the like;

(b) Benzodiazepines such as diazepam, lorazepam, clonazepam, clobazam, and the like;

(c) Barbiturates such as phenobarbital, amobarbital, methylphenobarbital, primidone, and the like;

(d) Valproates such as valproic acid, valproate semisodium, valpromide, and the like;

(e) GABA agents such as gabapentin, pregabalin, vigabatrin, losigamone, retigabine, rufinamide, SPD-421 (DP-VPA), T-2000, XP-13512, and the like;

(f) Iminostilbenes such as carbamazepine, oxcarbazepine, and the like;

(g) Hydantoins such as phenyloin sodium, mephenyloin, fosphenyloin sodium, and the like;

(h) NMDA antagonists such as harkoseramide, and the like;

(i) Sodium channel blockers such as BIA-2093, CO-102862, lamotrigine, and the like;

(j) Succinimides such as methsuximide, ethosuximide, and the like; and (k) AEDS such as acetazolamide, clomthiazole edisilate, zonisamide, felbamate, topiramate, tiagabine, levetiracetam, briveracetam, GSK-362115, GSK-406725, ICA-69673, CBD cannabis derivative, isovaleramide (NPS-1776), carisbamate, safinamide, seletracetam, soretolide, stiripentol, valrocemide, (2S)-(−)-N-(6-chloro-2,3-dihydro-benzo[1,4]dioxin-2-ylmethyl)-sulfamide, and the like.

In an embodiment, the anti-convulsant and/or anti-epileptic agent is selected from the group consisting of brivaracetam, carisbamate, carbamazepine, clobazam, clonazepam, ethosuximide, felbamate, gabapentin, lacosamide, lamotrigine, levetiracetam, oxcarbazepine, phenobarbital, phenyloin, pregabalin, primidone, retigabine, rufinamide, safinamide, seletracetam, talampanel, tiagabine, topiramate, valproate, vigabatrin, zonisamide, (2S)-(−)-N-(6-chloro-2,3-dihydro-benzo[1,4]dioxin-2-ylmethyl)-sulfamide, benzodiazepines, barbiturates and sedative hypnotics.

In another embodiment, the anti-convulsant and/or anti-epileptic agent(s) is selected from the group consisting of carisbamate, carbamazepine, clobazam, clonazepam, ethosuximide, felbamate, gabapentin, lamotrigine, levetiracetam, oxcarbazepine, phenobarbital, phenyloin, pregabalin, primidone, retigabine, rufinamide, talampanel, tiagabine, topiramate, valproate, vigabatrin, zonisamide and (2S)-(−)-N-(6-chloro-2,3-dihydro-benzo[1,4]dioxin-2-ylmethyl)-sulfamide.

In another embodiment, the anti-convulsant and/or anti-epileptic agent(s) is selected from the group consisting of carisbamate, carbamazepine, lamotrigine, phenobarbital, phenyloin, topiramate, valproate, zonisamide and (2S)-(−)-N-(6-chloro-2,3-dihydro-benzo[1,4]dioxin-2-ylmethyl)-sulfamide. Preferably, the anti-convulsant and/or anti-epileptic agent(s) is selected from the group consisting of carisbamate, carbamazepine, gabapentin, lamotrigine, levetiracetam, oxcarbazepine, phenyloin, pregabalin, valproate, topiramate and (2S)-(−)-N-(6-chloro-2,3-dihydro-benzo[1,4]dioxin-2-ylmethyl)-sulfamide. More preferably, the anti-convulsant and/or anti-epileptic is selected from the group consisting of carisbamate, gabapentin, lamotrigine, levetiracetam, valproate, topiramate and (2S)-(−)-N-(6-chloro-2,3-dihydro-benzo[1,4]dioxin-2-ylmethyl)-sulfamide.

In embodiments, the present invention provides methods of treating epilepsy and related disorders, regardless of underlying cause and/or stage of development, comprising administering to a subject in need thereof, an isolated form of a compound of formula (A) or pharmaceutically acceptable salt thereof, or an isolated form of an enantiomer of the compound of formula (A) or pharmaceutically acceptable salt thereof, alone or as co-therapy with one or more anticonvulsant or anti-epileptic agents, as described herein. The methods of this invention therefore provide the ability to suppress seizures, convulsions or the symptoms of an analogous seizure related disorder. In order to accomplish this objective the compounds or compositions of this invention must be used in the correct therapeutically effective amount or dose, as described below.

Optimal dosages and schedules to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The present invention further comprises pharmaceutical compositions containing an isolated form of a compound of formula (A), or an isolated form of an enantiomer of the compound of formula (A) or pharmaceutically acceptable salt thereof with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, an isolated form of a compound of formula (A), or an isolated form of an enantiomer of the compound of formula (A) or pharmaceutically acceptable salt thereof, as the active ingredients are intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01-5000 mg and may be given at a dosage of from about 0.01-100.0 mg/kg/day, or any range therein; preferably from about 0.1 to 70 mg/kg/day, or any range therein; more preferably from about 0.5-50 mg/kg/day, or any range therein; more preferably from about 1.0-30.0 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 5000 mg (or any range therein) of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of the present invention may also be carried out using a pharmaceutical composition comprising any of the compounds as defined herein and a pharmaceutically acceptable carrier. The pharmaceutical composition may contain between about 0.1 mg and 5000 mg, or any range therein, preferably about 50 to 2000 mg, or any range therein, of the active compound(s), and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Compounds of this invention may be administered in any of the foregoing compositions and according to dosage regimens established in the art whenever treatment of epilepsy or related disorders is required.

The daily dosage of the products may be varied over a wide range from 0.01 to 10,000 mg/kg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500, 1000, 200, 2500, 5000 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day or any range therein. Preferably, the range is from about 0.1 to about 70.0 mg/kg of body weight per day or any range therein; more preferably, from about 0.5 mg/kg to about 50 mg/kg, or any range therein; more preferably, from about 1.0 to about 30.0 mg/kg of body weight per day, or any range therein. The compounds may be administered on a regimen of 1 to 4 times per day.

Therapeutically effective dosage levels and dosage regimens for the anti-convulsant and anti-epileptic agents disclosed herein, may be readily determined by one of ordinary skill in the art. For example, therapeutic dosage amounts and regimens for pharmaceutical agents approved for sale are publicly available, for example as listed on packaging labels, in standard dosage guidelines, in standard dosage references such as the Physician's Desk Reference (Medical Economics Company) and other sources.

One skilled in the art will recognize that a therapeutically effective dosage of the compounds of the present invention can include repeated doses within a prolonged treatment regimen that will yield clinically significant results.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trails including first-in-human, dose ranging and efficacy trials, in healthy patients and/or those suffering from a given disorder, may be completed according to methods well known in the clinical and medical arts.

Determination of effective dosages is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

Preparation of the Compound of Formula (A)

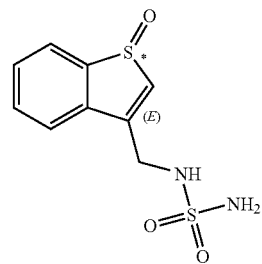

A 1-L 3-neck round bottom flask equipped with a magnetic stirrer, a thermocouple, a septum and nitrogen inlet adapter was charged with N-(benzo[b]thien-3-ylmethyl)-sulfamide (16.0 g, 66.03 mmol), dichloromethane (140 mL), and trifluoroacetic acid (100 mL; 1.31 mol) at 20° C. The resulting mixture was stirred for 5 min at 10° C., then hydrogen peroxide (6.2 mL; 70.49 mmol) was added dropwise over 2 min, and the reaction mixture stirred for 5 h while the reaction temperature was maintained between 8-10° C. in a cold water bath with addition of ice. Additional hydrogen peroxide (0.6 mL, 0.096 eq.) was added, and the reaction mixture was stirred for an additional hour at 10° C. A 1.5 M solution of sodium sulfite (2 mL; 3.00 mmol) was added at 0° C. and the resulting mixture stirred for 10 min. The solvents were removed in vacuo at 50° C., the resulting material was chased with methanol (30 mL×2) to yield the title compound as a yellowish waxy solid.

The yellowish waxy solid (24.1 g) was triturated with $CH_2Cl_2$/methanol (30/12 mL) to yield the title compound as a yellowish solid. This solid was triturated with ethyl acetate/methanol (90/10 mL) to yield the title compound as a racemate, as a slightly yellowish solid. The filtrates from both triturations were combined and concentrated to yield additional material, which was dissolved in $CH_2Cl_2$/methanol (15/15 mL), loaded on a $SiO_2$ column (900 g), and then eluted with (5% methanol/95% $CH_2Cl_2$+0.1% $NH_4OH$)×2 L, (8% methanol/92% $CH_2Cl_2$+0.1% $NH_4OH$)×2 L, (10% methanol/90% $CH_2Cl_2$+0.2% $NH_4OH$)×2 L to yield additional quantity of the title compound as an off-white solid.

1 HNMR (300 MHz, CD3OD) δ 7.95 (d, J=6.9 Hz, 1H), 7.74 (d, J=7.5 Hz, 1H), 7.75-7.56 (m, 2H), 7.18 (s, 1H), 4.31 (s, 2H), and 3.34 (s, variable H)

Example 2

Preparation of the Compound of Formula (A)

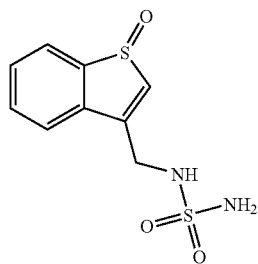

N-(benzo[b]thien-3-ylmethyl)-sulfamide (25 g, 103.17 mmol) was placed in a 1 L round-bottomed flask together with dichloromethane (175 mL, 2.73 moles) and trifluoroacetic acid (100 mL, 1.32 moles). Hydrogen peroxide (35 wt % in water; 10 mL, 114.52 mmol) was added to the resulting solution and the mixture stirred at room temperature for 3.5 h. The reaction was monitored by Thin Layer Chromatography (TLC) on silica gel plates using $CH_2Cl_2$/methanol (96:4) as eluent. The reaction mixture was treated with an aqueous solution $Na_2SO_3$ (1.5M; 3.75 mL, 0.05 equivalents) and the resulting mixture stirred for 15 min. The solvent was evaporated under reduced pressure at a temperature of 30° C. or lower to yield an oily residue. The residue was dissolved in $CH_2Cl_2$ (150 mL) and stirred at room temperature. Ethyl acetate (150 mL) was added slowly over about 2 h with stirring; a yellowish white solid precipitated during the addition. The resulting mixture was stirred overnight at room temperature under nitrogen, then cooled in an ice bath to 6° C. The solid was collected by filtration, washed with ethyl acetate and air-dried to yield the title compound as a solid.

Example 3

Chiral Separation of Compound of Formula (A) Racemate into Component Enantiomers

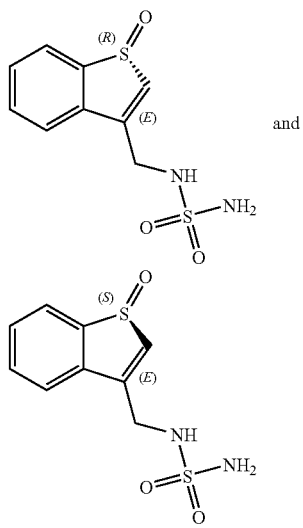

An analytical enantioselective chromatographic method was developed for the separation of the enantiomers of N-[(1-oxidobenzo[b]thien-3-yl)methyl]-sulfamide. Stationary phase Chiralpak ADH with methanol as a mobile phase was selected. Racemic compound was injected on a preparative enantioselective chromatographic column in methanol solution. Automated injections and collection cycles were repeated until the entire amount of the racemate was processed. Fractions containing individual enantiomers were collected during separation and evaporated to dryness.

When running the chromatographic separation, a low temperature of evaporation (5° C.) and a high vacuum (10 mbar), with temperature of the condenser set at −60° C. yielded single enantiomers with enantiomeric purity >95 ee and residual methanol content <1%. Absolute configuration of the single enantiomers was not determined.

Racemic (benzo[b]thien-3-ylmethyl]sulfamide S-oxide (8.0 g, Xli6-01-65 A3) was dissolved in methanol (80 mL) with sonication until a clear homogenous solution was formed. The solution was filtered through a 45 μm PVDF filter. The clear solution was stored at 4° C. The chiral separation was conducted with a Varian ProStar Preparative High Pressure Liquid Chromatography (HPLC) (detector model 330, pump model 215, autosampler model 410, fraction collector model 701), using a CHIRALPAK AD-H SFC column (ID 50 mm×250 mm, 5 micron). The sample (0.5 mL per injection) was introduced onto the column and eluted with methanol as the mobile phase at 50 mL/min, with UV monitoring at 235 nm.

Selected fractions from each sample injection were collected using a preparative fraction collector. Early eluting enantiomer (labeled EA) was collected in a time window of 8.4-8.8 min, racemic mixture in the peak valleys in a time window of 8.9-9.03 min, and late eluting enantiomer (labeled EB) in a time window of 9.04-10.0 min, into 200-mL bottles wrapped with aluminum foil in the dark. The fractions were then checked with chiral analytical HPLC (HP 1100, CHIRALPAK AD-H column, ID 4.6 mm×250 mm, 5 micron, with methanol (MeOH) as mobile phase and eluted at 0.5 mL/min under UV 220, 235, 254, 280 and 320 nm). Fractions containing isolated enantiomers were combined into a 2.5-L bottle and stored at 4° C. in the dark before concentration.

Fractions of separation were concentrated at 18-20° C. under high vacuum (Buchi vacuum pump V-700 with vacuum controller V-855, started at 235 mbar and gradually reduced to 1 mbar), and the resulting solid materials were stored at 4° C. after chiral analytic HPLC analysis confirmation.

After concentration of all early eluting (EA) enantiomer fractions, product was isolated as a white foamy solid (99% ee; 99.8% chemical purity, HPLC area %; 4.6% of the residual methanol, GC wt %) to yield the (+) enantiomer. Similarly, concentration of the EB enantiomer fractions yielded the (−) enantiomer as a slightly yellowish solid (92% ee; 98.1% chemical purity, HPLC area %; 0.54% of methanol, GC wt %). Circular dichroism detector response was positive (+) for the earlier eluted enantiomer, and negative (−) for the later eluted enantiomer. Measured optical rotations were as follows:

*EA* fraction: (+)-enantiomer=+1.11° (2.99 mg in 1 mL of methanol at 20° C. and 589 nm);

*EB* fraction: (−)-enantiomer=−1.10° (3.00 mg in 1 mL of methanol at 20° C. and 589 nm)

Enantiomer Stability Evaluation:

Samples of the isolated enantiomers were evaluated for stability using reversed phase column chromatography (to monitor the presence and/or absence of the test compounds and decomposition products) and chiral chromatography (to monitor racemization). The isolated enantiomers were stable to racemization and decomposition when suspended in methanol and Solutol HS 15 solutions (nontoxic polyoxyethylene esters of 12-hydroxystearic acid, available from BASF) for about 6.5 hours at room temperature. For the isolated compounds (solid phase), racemization and partial decomposition were observed during storage at room temperature. Additionally, forced temperature (60° C., overnight) and light degradation tests (light box, 5 hours) on the isolated enantiomers showed both racemization and decomposition.

NOTE: The (+) and (−) designations in the example above are intended to indicate the enantiomers based on their measured optical rotations. Exact stereo-configuration of the stereo-center of the above described enantiomers were not determined. One skilled in the art will further recognize that although the exact stereo-configuration was not determined (i.e. which of the two enantiomers is the (R) and which is the (S) enantiomer), the (R) and (S) enantiomers of the compound of formula (A) were nonetheless prepared and isolated according to the procedure as described herein in Example 3, which follows herein.

Example 4

In Vivo Assay: Maximal Electroshock Test (MES)

Anticonvulsant activity was determined using the MES test, run according to the procedure described in detail below. Swinyard E A, Woodhead J H, White H S, Franklin M R. Experimental selection, quantification, and evaluation of anticonvulsants. In Levy R H, et al., eds. *Antiepileptic Drugs*. 3$^{rd}$ ed. New York: Raven Press, 1989:85-102

CF-1 male albino mice (25-35 g) were randomly selected into control and test groups, with the animals dosed with vehicle or test compound, at varying time-points and concentrations, respectively. On the study date, the mice were dosed by intraperitoneal (i.p.) injection with vehicle (30% Solutol) or test compound (50-250 mg/kg). Seizures were induced by trans-corneal electric shock using a 60-Hz alternating current, 50 mA, delivered for 0.2 sec. The mice in the test groups were subjected to electrical stimulus at time intervals between 15 minutes and 4 hours following administration of test compound. The shock resulted in an immediate full body tonic extension. The test was complete when the entire course of the convulsion has been observed (typically, less than 1 minute after electrical stimulation).

Abolition of the full body tonic extensor component indicated that the test compound had the ability to prevent the spread of seizure discharge through neural tissue. The $ED_{50}$ value of the test compounds was the calculated dose required to block the hind limb tonic-extensor component of the MES-induced seizure in 50% of the rodents tested. A probit analysis was used to calculate the $ED_{50}$ and 95% confidence interval.

Representative compounds of the present invention were tested according to the procedure described above, with results as listed in Table 1 below. Results are listed as (number of mice with full body tonic extension prevented)/(total number of mice tested) (@ a given time). $ED_{50}$ values were determined at the time of peak effect (1 hr, Table 1).

TABLE 1

| Compound/Dosage | MES Activity | | | | |
|---|---|---|---|---|---|
| | 0.25 Hrs | 0.50 Hrs | 1.0 Hrs | 2 Hrs | 4 Hrs |
| Vehicle | 0/5 | | 0/5 | | |
| (+)-enantiomer/ 200 mg/kg | 0/3 | 4/5 | 5/5 | 5/5 | 1/5 |
| (+)-enantiomer/ 100 mg/kg | | | 1/4 | 0/4 | |
| (−)-enantiomer/ 200 mg/kg | 1/4 | 2/5 | 5/5 | 5/5 | 1/5 |
| (−)-enantiomer/ 100 mg/kg | | | 2/4 | 1/4 | |

(+)-enantiomer, $ED_{50}$ = 127 mg/kg (95% at 104 mg/kg and CI = 160 mg/kg
(−)-enantiomer, $ED_{50}$ = 126 mg/kg (95% at 100 mg/kg and CI = 163 mg/kg

Example 5

As a specific embodiment of an oral composition, 100 mg of the compound prepared as in Example 1 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. An isolated form of a compound having the formula (A)

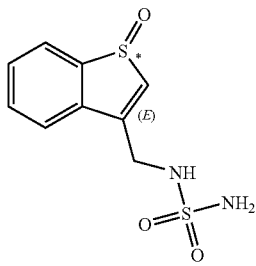

or an enantiomer or pharmaceutically acceptable salt thereof.
2. A substantially pure compound as in claim 1.
3. A pharmaceutical composition comprising a pharmaceutically acceptable carrier and a compound of claim 1.
4. A pharmaceutical composition made by mixing a compound of claim 1 and a pharmaceutically acceptable carrier.
5. A process for making a pharmaceutical composition comprising mixing a compound of claim 1 and a pharmaceutically acceptable carrier.
6. An isolated compound as in claim 1, having a (+) optical rotation.
7. A substantially pure compound as in claim 6.
8. An isolated compound as in claim 1, having a (−) optical rotation.
9. A substantially pure compound as in claim 8.
10. A method of treating epilepsy, comprising administering to a subject in need thereof a therapeutically effective amount of the compound of claim 1.
11. A method for treating epilepsy, comprising administering to a subject in need thereof, a therapeutically effective amount of co-therapy with a compound as in claim 1 and one or more anti-epileptic or anti-convulsant agents.
12. The method of claim 11, wherein the disorder is epilepsy.
13. The method of claim 11, wherein the anti-convulsant or anti-epileptic agent is selected from the group consisting of carisbimate, carbamazepine, clobazam, clonazepam, ethosuximide, felbamate, gabapentin, lamotrigine, levetiracetam, oxcarbazepine, phenobarbital, phenyloin, pregabalin, primidone, retigabine, rufinamide, talampanel, tiagabine, topiramate, valproate, vigabatrin, zonisamide, (2S)-(−)-N-(6-chloro-2,3-dihydro-benzo[1,4]dioxin-2-ylmethyl)-sulfamide, benzodiazepines, barbiturates and sedative hypnotics.
14. The method of claim 13, wherein the anti-convulsant or anti-epileptic agent is selected from the group consisting of carisbimate, carbamazepine, clobazam, clonazepam, ethosuximide, felbamate, gabapentin, lamotrigine, levetiracetam, oxcarbazepine, phenobarbital, phenyloin, pregabalin, primidone, retigabine, rufinamide, talampanel, tiagabine, topiramate, valproate, vigabatrin, zonisamide and (2S)-(−)-N-(6-chloro-2,3-dihydro-benzo[1,4]dioxin-2-ylmethyl)-sulfamide.
15. The method of claim 14, wherein the anti-convulsant or anti-epileptic agent is selected from the group consisting of carisbimate, carbamazepine, gabapentin, lamotrigine, levetiracetam, oxcarbazepine, phenyloin, pregabalin, valproate, topiramate and (2S)-(−)-N-(6-chloro-2,3-dihydro-benzo[1,4]dioxin-2-ylmethyl)-sulfamide.

* * * * *